US008300229B2

(12) United States Patent
Cho et al.

(10) Patent No.: US 8,300,229 B2
(45) Date of Patent: *Oct. 30, 2012

(54) CHEMICAL SENSING WITH COHERENT DETECTION OF OPTICAL SIGNAL

(75) Inventors: Pak Shing Cho, Gaithersburg, MD (US); Geoffrey Harston, Laurel, MD (US)

(73) Assignee: CeLight, Inc., Silver Spring, MD (US)

( * ) Notice: Subject to any disclaimer, the term of this patent is extended or adjusted under 35 U.S.C. 154(b) by 126 days.

This patent is subject to a terminal disclaimer.

(21) Appl. No.: 12/635,848

(22) Filed: Dec. 11, 2009

(65) Prior Publication Data

US 2012/0002211 A1    Jan. 5, 2012

Related U.S. Application Data

(63) Continuation-in-part of application No. 12/361,664, filed on Jan. 29, 2009, now Pat. No. 8,009,294, and a continuation-in-part of application No. 11/938,655, filed on Nov. 12, 2007, now Pat. No. 7,801,395, and a continuation-in-part of application No. 11/695,920, filed on Apr. 3, 2007, now Pat. No. 7,715,720.

(51) Int. Cl.
*G01B 9/02* (2006.01)
*G01J 3/45* (2006.01)

(52) U.S. Cl. ...................................... 356/451
(58) Field of Classification Search .................. 356/128, 356/432, 451, 484, 517
See application file for complete search history.

(56) References Cited

U.S. PATENT DOCUMENTS

| | | | | |
|---|---|---|---|---|
| 5,027,436 A | * | 6/1991 | Delavaux | 398/202 |
| 6,709,857 B2 | * | 3/2004 | Bachur, Jr. | 435/288.7 |
| 7,277,178 B2 | * | 10/2007 | Shpantzer et al. | 356/451 |
| 7,327,913 B2 | * | 2/2008 | Shpantzer et al. | 385/15 |
| 7,426,035 B2 | * | 9/2008 | Shpantzer | 356/451 |
| 7,483,600 B2 | * | 1/2009 | Achiam et al. | 385/14 |
| 7,502,118 B2 | * | 3/2009 | Shpantzer | 356/451 |
| 7,801,395 B2 | * | 9/2010 | Shpantzer et al. | 385/14 |
| 2009/0236528 A1 | * | 9/2009 | Shpantzer et al. | 250/339.07 |

* cited by examiner

*Primary Examiner* — Michael A Lyons
(74) *Attorney, Agent, or Firm* — Nadya Reingand

(57) ABSTRACT

This invention relates generally to the systems and methods for standoff trace chemicals detection such as explosives residue and others, and particularly to optical devices and the methods of their use based on sensing of gases and residue materials. This sensing includes detection and measurement of optical absorption spectra and relative concentration of the chemical followed by the chemical identification based on these spectral data. The sensing is based on photothermal interferometry method improved by implementation of coherent optical detection. The coherent optical detection is performed by an integrated polarization-diversity coherent receiver with an electro-optic phase modulator for a local oscillator optical beam. The implementation of pulsed probe sensing and local oscillator optical beams in the coherent detection improves the device with better eye safety performance. The hybrid calibration via a phase-modulated local oscillator optical beam allows optimizing the signal reception and reduces complexity of the probe subsystem.

20 Claims, 6 Drawing Sheets

(a)

(b)

(a)

(b)

CHEMICAL SENSING WITH COHERENT DETECTION OF OPTICAL SIGNAL

CROSS-REFERENCE TO RELATED APPLICATIONS

This application is a continuation-in-part of U.S. Ser. No. 12/361,664 filed Jan. 29, 2009 now U.S. Pat. No. 8,009,294, Ser. No. 11/938,655, filed Nov. 12, 2007, currently U.S. Pat. No. 7,801,395, and Ser. No. 11/695,920, filed Apr. 3, 2007, currently U.S. Pat. No. 7,715,720, all of which applications are fully incorporated herein by reference.

FIELD OF INVENTION

This invention relates generally to systems and methods for chemical detection such as explosives and others, and more particularly to photothermal interferometric spectroscopy devices, and their methods of use, based on optical signal detection.

BACKGROUND OF THE INVENTION

The principles of photothermal spectroscopy are generally described in a publication by Stephen E. Bialkowski entitled "Photothermal Spectroscopy Methods for Chemical Analysis", John Wiley & Sons, Inc., 1996, the entire content of which is incorporated by reference herein. Photothermal spectroscopy method provides sensitive measurements of optical absorption in homogeneous and inhomogenous media.

McLean et al. (E. A. McLean et al. American Journal Applied Physics Letters, 13, p. 369 (1968)) recognized that the optical absorption resulting in sample heating and subsequent changes in refractive index would cause a phase shift in light passing through the heated region. This phase shift can be detected by interferometric means.

Grabiner et al. (F. R. Grabiner et al. Chemical Physics Letters, 17, p. 189 (1972)) proposed to use two lasers for photothermal interferometric spectroscopy: pulsed infrared laser for the medium excitation and visible probe laser for the refractive index change measurement.

In the U.S. Pat. No. 6,709,857 a system and method for monitoring the concentration of a medium using photothermal spectroscopy is disclosed. The system and method each employs an energy emitting device, such as a laser or any other suitable type of light emitting device, which is adapted to emit a first energy signal toward a location in the container. The first energy signal has a wavelength that is substantially equal to a wavelength at which the medium absorbs the first energy signal so that absorption of the first energy signal changes a refractive index of a portion of the medium. The system and method each also employs a second energy emitting device, adapted to emit a second energy signal toward the portion of the medium while the refractive index of the portion is changed by the first energy signal, and a detector, adapted to detect a portion of the second energy signal that passes through the portion of the medium. The system and method each further employs a signal analyzer, adapted to analyze the detected portion of the second energy signal to determine an amount of a sample in the container based on a concentration of the medium in the container.

There is a need for reliable remote methods and systems for detecting the presence of chemicals in the field. When the probe light illuminates a chemical located far away from the detector, the collected portion of the beam, which carries information about the chemical, has low intensity. There is a need to provide highly sensitive receivers to improve signal-to-noise ratio of the detected signal, which gives an opportunity to detect chemicals remotely.

SUMMARY OF THE INVENTION

Accordingly, an object of the present invention is to provide improved methods and systems directed to chemical detection, such as explosives and the like, at remote location, including explosive residue on a surface. The system and method are based on the use of photothermal interferometric spectroscopy, which includes illumination of the chemical by a strobe beam followed by reading-out the information about the chemical concentration by a probe beam. The strobe beam has a spectral energy band across at least a portion of a characteristic absorption band of the chemical, and its energy is absorbed by molecules of the chemical. This leads to a change of refractive index, which is sensed by the probe beam. The probe beam is mixed with a local oscillator (LO) beam at a coherent receiver, and the probe and the local oscillator beam are pulsed beams with the same rate. The duration of the pulses in the local oscillator beam is selected to achieve the best SNR in the detected signal and the lowest duty cycle. The coherent optical receiver carries out homodyne detection of the incoming probe beam.

A distance to the remote location of the chemical from the probe unit is determined by a range finder; the distance is applied to an adjustable fiber delay-line network to match arrival times of the incoming probe beam and the local oscillator beam at the coherent optical receiver in order to maximize SNR.

Yet another object of the present invention is to provide a coherent optical receiver, which includes a 90-degrees optical hybrid for mixing the probe and the LO beams. The 90-degrees optical hybrid is calibrated prior to the system operation and optionally periodically calibrated during the system exploitation.

Yet another object of the present invention is to provide a polarization-diversity coherent optical receiver. The polarization-diversity coherent optical receiver includes two inputs for incoming probe beams having orthogonal polarization states, an input for the LO beam, an electro-optic phase modulator for optical phase modulation of the LO beam, a polarization beam splitter receiving the phase-modulated LO beam and splitting it into two beams with orthogonal polarization states; two optical hybrids each operating on one polarization state of light; each hybrid having two inputs, one for the probe beam and one for the LO beam, and four outputs. The polarization-diversity receiver of the preferred embodiment is a monolithic integrated device.

Yet another object of the present invention is a method for determining information about a chemical. A strobe beam with one or more wavelengths that are in absorption band of the chemical is directed to a location where the chemical is present. It interacts with the chemical changing its refractive index. A probe beam is directed to the same location, and its phase changes due to the change of the refractive index. At the receiver, the probe beam is mixed with a local oscillator beam, both being pulsed beams with the same rate. The phase shift measuring allows obtaining information about at least one of, absorption spectrum and concentration of the chemical. The pulse duration of the probe beam is selected to achieve the best SNR in the detected signal and the lowest duty cycle. The pulse duration of the local oscillator beam is comparable but not shorter than the pulse duration of the receiving beam at the receiver. The mixing is performed in a 90-degrees optical hybrid. In the preferred method, the hybrid is calibrated prior to its operation and optionally periodically during the exploitation.

DETAILED DESCRIPTION OF THE PREFERRED EMBODIMENT

The present invention now will be described more fully hereinafter with reference to the accompanying drawings, in which the preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

One embodiment of the present invention is a multi-modal spectroscopy system. The system acquires the target and remotely senses the presence of explosive residues via their unique direct light absorption (MWIR mode) and/or stimulated Raman induced absorption (LWIR mode) signatures. In operation, a tunable pulsed laser subsystem strobes the surface molecules inducing an abrupt minute change in the refractive index of the target. This in turn results in a phase change in the returned probe laser beam that is measured by the co-located analyzer receiving system. The analyzer consists of novel digital coherent pulsed interferometer that is capable of extracting the signal-derived phase change from air-turbulence, target movement and vibration. The excitation laser can be produced by an Optical Parametric Oscillator (OPO) or quantum cascaded lasers (QCLs).

The system and method of the present invention provide a tool for standoff detection of vapor chemicals and chemical residues on a surface with a special interest to trace explosives detection.

Figure 1:
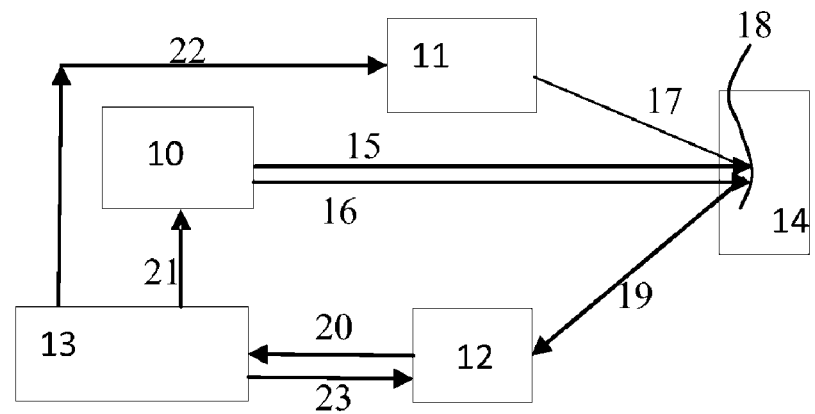
FIG. 1 is a block diagram of a photothermal interferometric spectroscopy system of the present invention: (a) with reflected probe beam, (b) with transmitted probe beam.
Figure 1:
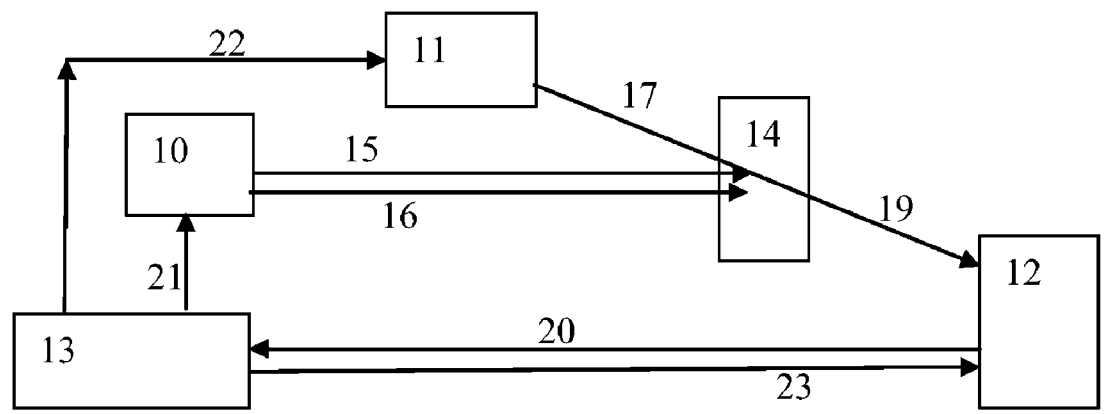

In one embodiment of the present invention, an optical device is provided, the block diagram of which is shown in FIG. 1(a), where 10 is a unit that combines strobe generation and targeting, 11 is the unit for optical probe beam generation and targeting, 12 is a signal detection and recovery block, and 13 is electronics control and processing block.

The LWIR band exploits the information rich of 6-8 μm wavelength range resulting in enhanced sensitivity and selectivity towards nitrogen-containing explosives. In general, Raman features in the 6-8 μm region are highly specific and unique. Stimulated Raman induced absorption can be accomplished using two spatially and temporally overlapping transmitted near IR laser beams at the surface residue target 14 [Reference: J. J. Barrett and D. F. Keller, "Theoretical analysis of photoacoustic Raman spectroscopy," Journal of Optical Society of America, vol. 71, 1981, p. 1299.]. Specifically, a pump 15 and an idler 16 beams that are eye-safe and suffer negligible attenuation in the atmosphere at ranges up to 30 m. Stimulated Raman (SR) offers better selectivity and specificity over the direct MWIR absorption approach for identifying explosives surface residues against background interferents.

In the preferred embodiment the strobe beam wavelengths can change its wavelength between the first wavelength to the second wavelength within 1 msec, which corresponds to the frequency of change up to kHz.

The chemical under study is also illuminated by a probe beam (this beam is called "the second beam") or a set of beams 17 coming from the light source located in the probe unit 11. In the preferred embodiment of the present invention, shown in FIG. 1(a), the probe set of beams is reflected by the reflection surface 18.

The light beam 19 reflected from the surface 18 is received by the signal detection and recovery block 12 and then the electrical output 20 is forwarded to the control unit 13. In the preferred embodiment the signal detection is performed in the coherent receiver as described in the U.S. patent application Ser. No. 10/938,655 "Optical coherent detector and optical communications system and method" by I. Shpantzer et al, incorporated herein by reference.

The unit 13 controls the operation of the probe beam generation via control signal 21, the strobe beam generation via control signal 22 and the receiver performance via control signal 23.

The disclosed PTI method is applicable to detect both trace vapors and chemical residues on solid surfaces. In case of vapors, the examined chemical volume 14 is right in front of the reflecting surface 18. In case of chemical residues, both the strobe and the probe lasers are focused on the interrogated surface 14.

It is another embodiment of the present invention is a system operating without the background reflection surface. The background surface can be eliminated if there is enough back scattered light in the interrogated chemical volume to carry out the detection.

FIG. 1(b) shows another embodiment of the present invention. This is the analogous scheme for the chemicals detection, but operating in the transmission mode. In certain situations it could be possible to install the light transmitter 11 and detector 12 on the opposite sides of the interrogated chemical volume 19. This allows the chemical detecting without background reflection surface.

The detected molecules can be brought into the excited state from which it relaxed by the following processes: (i) direct one-photon absorption; (ii) two-photons stimulated Raman absorption. The high selectivity of stimulated Raman absorption provides better specificity against background interference. It also enables the use of less exotic light sources that simplify and optimize the overall system.

Figure 2:
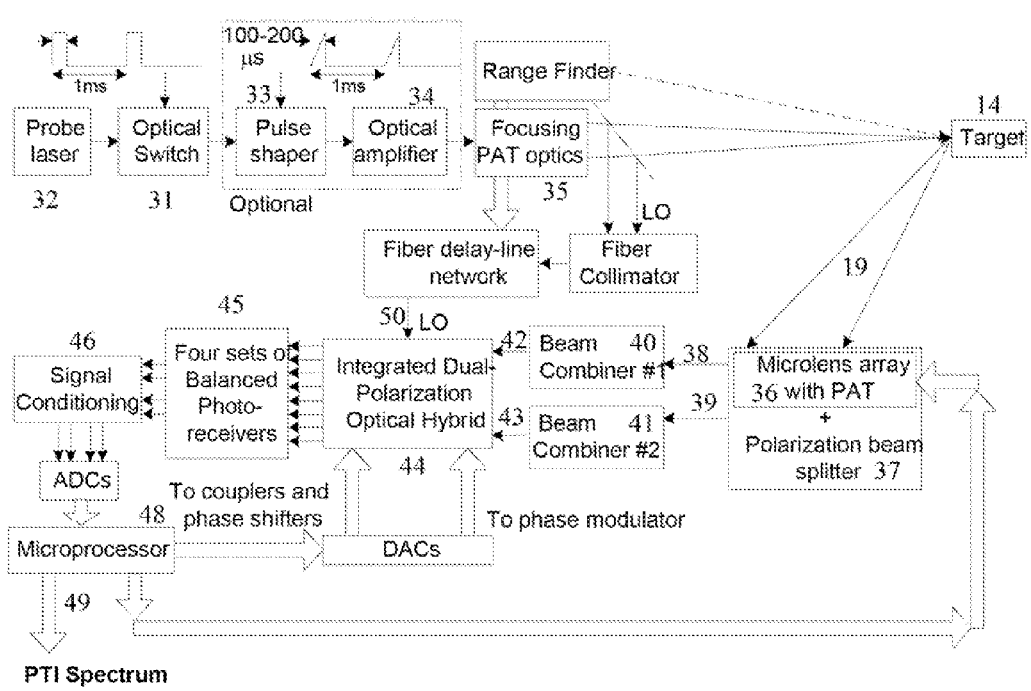
FIG. 2 is a schematic diagram of the chemical detection system operating on two polarization states of light.

The preferred embodiment of the probe subsystem architecture is shown in FIG. 2. The optical switch 31 shapes the output of the probe laser 32. This beam can be further modified by the pulse shaper 33 and optical amplifier 34. The beam is focused on the target 14 by the focusing pointing-acquisition-tracking (PAT) unit 35. A range finder, part of the unit 35, determines the distance between the transmitter and the target. The distance information is supplied to an adjustable fiber delay-line network to match the arrival time of the LO and received signal beam at the optical hybrid. This suppresses the impact of the probe laser frequency and phase noise on the homodyne detected signal thereby increasing the SNR. The reflected beam 20 is collected by a set of microlenses 36 with PAT and split into two beams with orthogonal polarizations 37. The beams 38 and 39 with orthogonal polarization state enter beam combiners 40 and 41. The combiners were described in details in U.S. patent application Ser. Nos. 12/361,664 filed Jan. 29, 2009 and 12/389,803 filed Feb. 20, 2009 by the same legal entity. The outputs of the beam combiners 42 and 43 enter dual polarization optical hybrid 44. The hybrid 44 has been described in details in U.S. patent application Ser. No. 12/413,161 filed Mar. 27, 2009 by the same legal entity. Four balanced receivers 45 convert eight optical signals into four electrical signals, which are further processed in the conditioning unit 46, ADCs 47 and microprocessor 48. The output spectrum 49 of the interrogated chemical can be displayed or used for further processing.

The microprocessor 48 also controls the operation of the optical hybrid 44, which will be described in more details in the following paragraphs. The microprocessor 48 also controls the beam combining unit 36.

Figure 3:
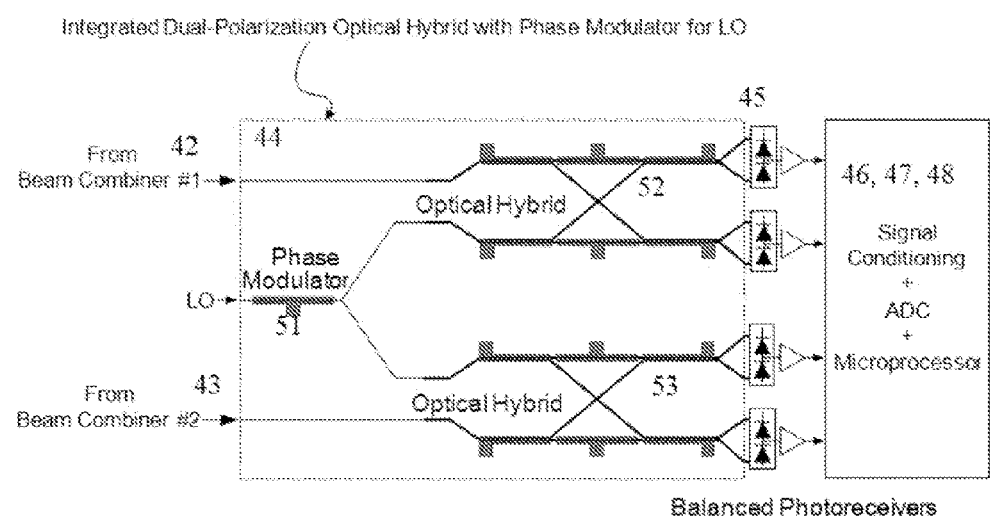
FIG. 3 is a schematic diagram of a polarization diversity optical receiver of the present invention.

In one embodiment, the hybrid 44 combines incoming optical beams 42 and 43 with the local oscillator beam 50. It is preferable that the LO beam is formed as a part of the beam coming from the probe laser 32. The polarization-diversity optical receiver operation is shown in more details in FIG. 3 depicting an integrated version of the receiver with two optical hybrids, an input optical waveguide for the LO, a electro-optic phase modulator 51 for optical phase modulation of the LO, and a Y-branch waveguide that divides the phase-modulated LO into the second input waveguides of the two hybrids.

The receiver includes two 90-degrees optical hybrids 52, 53 and four sets of balanced photodetectors 45. Two incoming optical signals S (42 and 43) are mixed with signals from the local oscillator L. The resulting four output signals from each optical hybrid have 90 degrees relative phase difference of the form: A=S+L, B=S−L, C=S+jL and D=S−jL.

In the preferred embodiment both signal beam and LO beam are pulsed optical signals, generated by a CW light source 30, an optical switch with high extinction ratio and shaped by an optical modulator. This arrangement is beneficial for the present chemical sensing system. The pulsed probe signal with a low duty cycle for the interrogated object illumination is potentially safer for eyes than the use of CW light source of the same peak power. Pulsed laser with low duty cycle also reduces undesirable heat build-up and thermal effect on the interrogated absorbing object. The optical switch produces an optical pulse train with adjustable pulse width and pulse repetition rate. The optical modulator provides a mean to shape the optical power profile of the probe pulse that minimizes the impact of the erbium-doped fiber amplifier gain dynamic response on the probe laser pulse.

Figure 4:
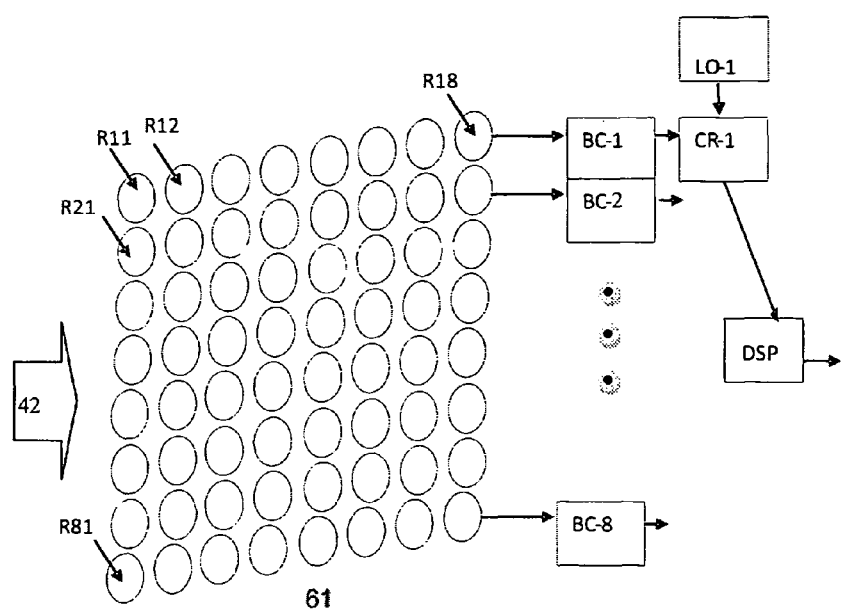
FIG. 4 is a block diagram of a large area beam receiver according to the present invention.

In the preferred embodiment the signal beams 42, 43 are the result of light collection from a relatively large area with the use of phase distortion correction over the field of view (FIG. 4). A matrix of collecting lenses 61 is followed by Row Beam combiners BC-1-BC-8, followed by a set of coherent receivers CR (FIG. 4 shows only the first coherent receiver CR-1 from the whole column of the coherent receivers) and digital signal processing unit DSP. In one embodiment, the lenses in the matrix are placed in rows (the first row is formed by the lenses R11, R12 . . . R18) and columns (the first column is formed by the lenses R11, R21 . . . R81). This optical beam combiner was described in details in U.S. patent application Ser. No. 12/389,803 filed Feb. 20, 2009 by the same legal entity; it is fully incorporated herein by reference.

Figure 5:
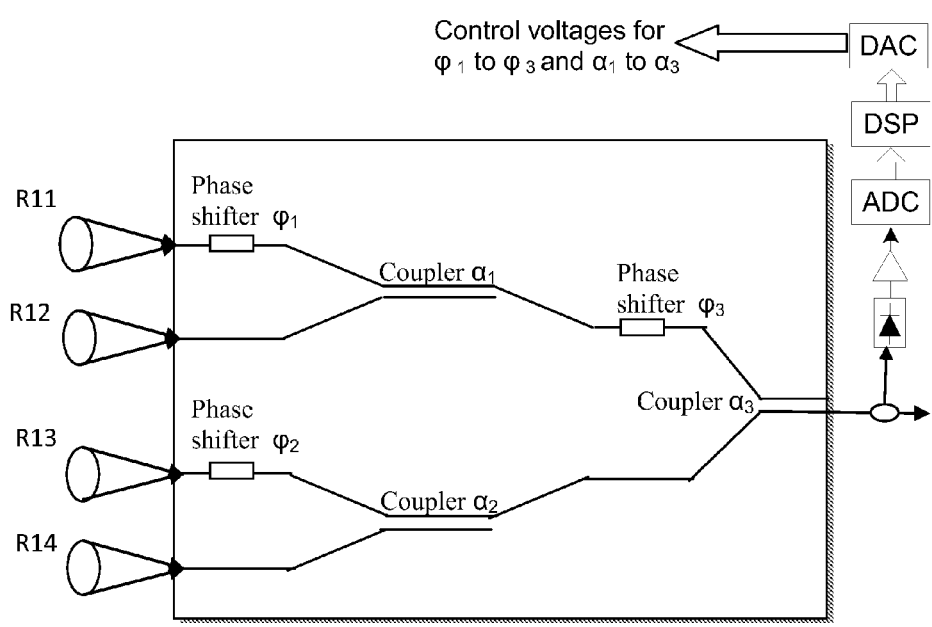
FIG. 5 shows large area beam combining in the optical receiver of the present invention.

The light, received by a row of lenses, is inserted into waveguides of the combiner. For example, the light from lenses R11-R 18 is inserted in input waveguides of the combiner BC-1. FIG. 5 provides more details on the $2^M$ input combiner structure (M=2 as an example). Such an optical device has $2^M$ input waveguides (M is an integer 1), each receiving a portion of the incoming optical beam. The waveguides are connected by ($2^M$-1) directional couplers forming a tree-like structure; each coupler is formed by two waveguides, coming in and out of the coupler. In the preferred embodiment, the directional coupler is a two-section coupler with an alternating or reversed $\Delta\beta$. $\Delta\beta$ is the mismatch of the propagation constants of the two coupling waveguides that form the directional coupler. In each coupler one of the two input waveguides has a phase shifter for changing an input phase of the optical beam portion in the same waveguide before its coupling. Furthermore, the power coupling ratio of each ($2^M$-1) directional couplers can be adaptively adjusted in respond to the optical beams in the two input waveguides. The output waveguide forms an input waveguide for a subsequent coupler from ($2^M$-1) couplers. A final output waveguide from the last coupler is a final output beam of the device. The control means operate to change the phases of the beams propagating in the waveguides before their coupling as well as to change the coupling ratio of the coupler. This change aims to maximize the final output beam power. The control means may include a photodetector receiving a beam in the final output waveguide, producing an electrical signal proportional to the output optical power. The coupling ratio of the coupler as well as the input phase of the optical beam portion in the same waveguide before its coupling is adjusted in a manner that maximizes the output optical power in the final output waveguide. The input phase is changed in a phase shifter connected to the same waveguide before coupling. The coupling ratio is changed in the coupler itself.

It is another object of the present invention to provide stabilized performance of the polarization-diversity optical receiver of FIG. 3. The optical hybrid calibration is carried out prior to the chemical sensing procedure. The hybrid calibration is similar to the one disclosed in U.S. patent application Ser. No. 11/938,655 by the same legal entity which is fully incorporated herein by reference. One significant difference with the procedure disclosed in Ser. No. 11/938,655 is that the signal probe beam in the PTI system is not modulated, instead the local oscillator is phase modulated during hybrid calibration. The local oscillator beam is modulated using in an electro-optic phase modulator 51 (FIG. 3); full optical phase modulation of the local oscillator is achieved with the phase modulator that is driven through at least 360 degree phase shift. The driving signal to the phase modulator can be a ramp, sinusoidal, or other periodic waveform.

Figure 6:
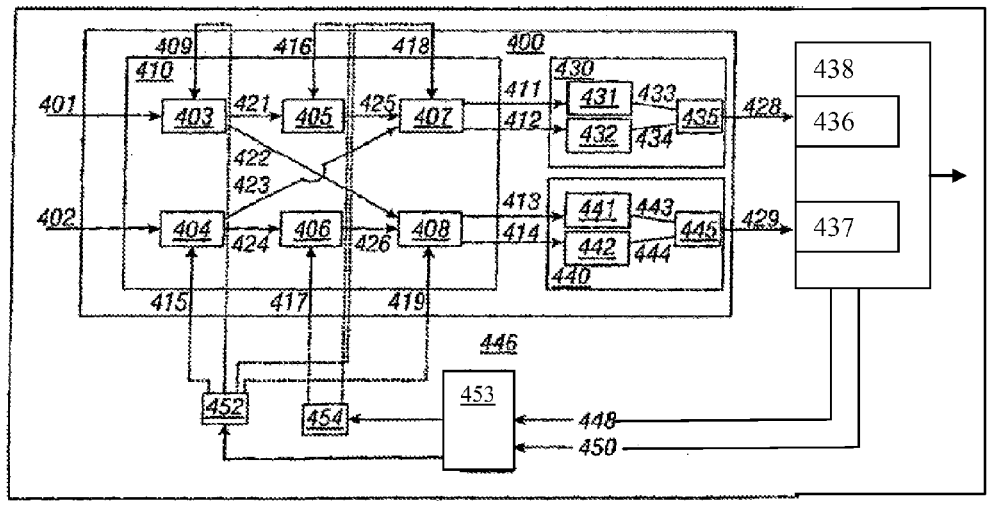
FIG. 6 shows calibration of the coherent optical receiver using fast ADCs.

The calibration procedure of the optical hybrid 410 is shown in FIG. 6; it includes the following. For directional coupler 403, equal splitting of light energy of the incoming signal beam 401 into outputs 421 and 422 can be achieved by controlling the 'coupler phase' via control line 409. For directional coupler 404, equal splitting of light energy of the incoming local oscillator beam 402 into outputs 423 and 424 can be achieved by controlling the 'coupler phase' via control line 415. For directional coupler 407, equal splitting of light energy into outputs 411 and 412 can be achieved by controlling the 'coupler phase' via control line 418. And for directional coupler 408, equal splitting of light energy into outputs 413 and 414 can be achieved by controlling the 'coupler phase' via control line 419. Output beams 411-414 of the hybrid 410 are transformed into electrical signals 433-434 and 443-444 by the photodetectors 431-432 and 441-442 respectively. Differential detectors 430 and 440 also include Transimpedance Amplifiers (TIAs) 435 and 445 for the signals processing.

For phase shifters 405 and 406, 90-degrees relative phase difference between inputs 423 and 425 (e.g. S and L) and 422 and 426 (e.g. S and jL) can be achieved by controlling the phase shift parameters via control lines 416 and 417.

Figure 7:
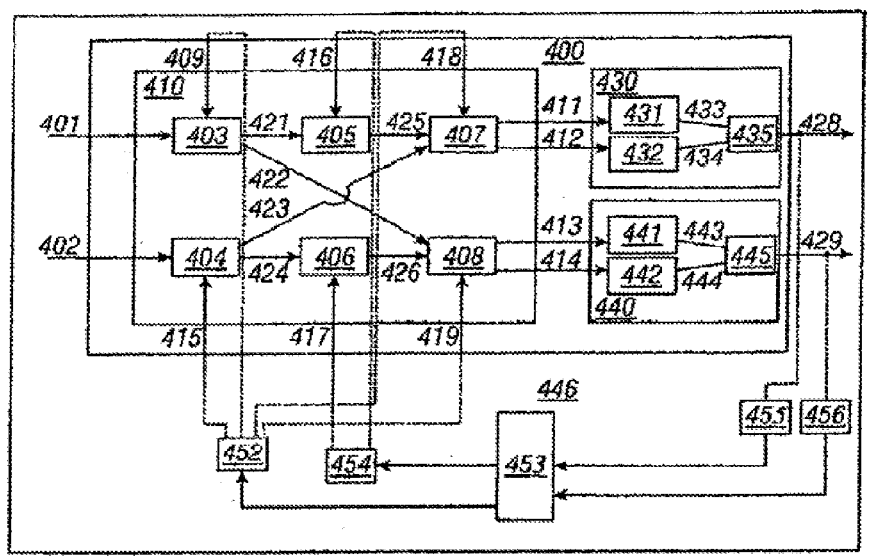
FIG. 7 shows calibration of the coherent optical receiver using signal tapped from the outputs.

Coherent receiver 400 can be calibrated digitally, as FIG. 6, or in a manner as illustrated in FIG. 7 with the calibration block marked as 446. Referring to FIG. 6, coherent receiver 400 is digitally calibrated. Coherent detector outputs 428 and 429 can be connected to two fast (symbol rate) A/D converters 436 and 437, being a part of a processing unit 438, for further digital signal processing. Digital samples 448 and 450 are processed by processor 453.

In another implementation, the detector analog outputs 428 and 429 (FIG. 7) can be tapped and sampled by two A/D converters 455 and 456. The A/D outputs are directed to processor 453. These A/D converters 455 and 456 can have sample rates lower than the rates of A/D converters 436, 437 operating in the scheme of FIG. 6.

Processor 453 collects samples of inputs 448 and 450, and estimates their statistical properties, and performs the control algorithms as described below.

The algorithm results are applied to a set of controllers. The processor controls the coupler phases via the coupler phase controller 452. The phase shifts are controlled by 454.

The following algorithm can be utilized to track the coupler phase of 407, 408, 403 and 404. Again, the present invention is not limited to these algorithms, which are presented by way of example and without limitation.

To track the coupler phase of 407, 408, 403 and 404, the following can be utilized:
1. Adjust control line 418 via controller 452, to maximize the variance or minimize the mean of output 428.
2. Adjust control line 419 via controller 452, to maximize the variance or minimize the mean of output 429.
3. Adjust control lines 409 and 415 so that the variance of output 428 is equal to the variance of output 429, while
4. Maximizing the sum of the two variances at outputs 428 and 429.

The following algorithm can be utilized to maintain the phase of both phase shifters 405 and 406. Again, the algorithms are provided by way of examples and without limitation. To maintain the phase of both phase shifters 405 and 406, the following can be utilized:
1. Adjust control lines 416 and 417 at the same time via controller 454, to cancel the covariance of the two outputs 428 and 429.

The description of a preferred embodiment of the invention has been presented for purposes of illustration and description. It is not intended to be exhaustive or to limit the invention to the precise forms disclosed. Obviously, many modifications and variations will be apparent to practitioners skilled in this art. It is intended that the scope of the invention be defined by the following claims and their equivalents.

What is claimed is:

1. A system for detecting a chemical at a remote location, comprising:
   a first laser configured to irradiate a strobe beam with a spectral energy band across at least a portion of a characteristic absorption band of the chemical;
   a probe unit configured to irradiate the chemical with a probe beam and interferometrically sense and measure the absorption of the strobe beam by molecules of the chemical and determine a concentration of the chemical;
   the probe unit including a coherent optical receiver, which mixes an incoming probe optical beam with a local oscillator (LO) beam, wherein the probe and the local oscillator beam are pulsed beams with the same pulse rate.

2. The system of claim 1, wherein a duration of the pulses in the local oscillator beam is selected to achieve a best SNR in a detected signal and a lowest duty cycle.

3. The system of claim 1, wherein a distance to the remote location of the chemical from the probe unit is determined by a range finder; the distance being applied to the local oscillator beam via an adjustable fiber delay-line network to match arrival times of the incoming probe beam and the local oscillator beam at the coherent optical receiver in order to maximize SNR.

4. The system of claim 1, wherein the coherent optical receiver carries out homodyne detection of the incoming probe beam.

5. The system of claim 1, wherein the coherent optical receiver includes a 90-degree optical hybrid.

6. The system of claim 5, wherein the 90-degree optical hybrid is calibrated prior to beginning of an operation of the system and optionally periodically calibrated during exploitation of the system.

7. The system of claim 5, wherein four couplers of the 90-degree-optical hybrid are calibrated by adjusting a coupling ratio of the couplers to minimize the mean of one of output signals I and Q from the optical hybrid and then to maximize a sum of two variances at outputs.

8. The system of claim 5, wherein phase shifters of the 90-degree optical hybrid are calibrated by adjusting both phases at the same time to cancel a covariance of two outputs I and Q.

9. The system of claim 1, wherein the receiver is a polarization-diversity coherent optical receiver.

10. The system of claim 9, wherein the polarization-diversity coherent optical receiver includes two inputs for incoming probe beams having orthogonal polarization states, an input for the LO beam, an electro-optic phase modulator for optical phase modulation of the LO beam, a polarization beam splitter receiving the phase-modulated LO beam and splitting it into two beams with orthogonal polarization states; two optical hybrids each operating on one polarization state of light; each hybrid having two inputs, one for the probe beam and one for the LO beam, and four outputs.

11. The system of claim 10, wherein the polarization-diversity coherent optical receiver is a monolithic integrated device.

12. The system of claim 1, wherein the chemical is in the form of a gas, liquid or solid, including explosives.

13. The optical system of claim 1, wherein the strobe beam consists of coherent pulses.

14. A method for determining information about a chemical, comprising:
   directing a strobe beam to a location where the chemical is present, the strobe beam having one or more wavelengths that are in absorption spectrum of the chemical, wherein the strobe beams interacts with the chemical changing its refractive index;
   directing a probe beam to interact with the chemical;
   receiving at a coherent receiver at least a portion of the probe beam passed through the chemical, a phase of this probe beam being changed due to the change of the refractive index;
   mixing the received probe beam with a local oscillator beam, both being pulsed beams with the same pulse rate, and measuring a phase shift of the received beam being indicative of at least one of absorption spectrum and concentration of the chemical.

15. The method of claim 14, wherein the chemical is located remotely from light sources for the strobe and probe beams and the receiver at a distance from 1 meter to 1000 meters.

16. The method of claim 14, wherein a pulse duration of the local oscillator beam is comparable but not shorter than a pulse duration of the received probe beam.

17. The method of claim 14, wherein the pulse duration of the received probe beam is selected to achieve a best SNR in a detected signal and a lowest duty cycle.

18. The method of claim 14, wherein the mixing is performed in a 90-degree optical hybrid.

19. The method of claim 18, wherein the 90-degree optical hybrid is calibrated prior to its operation and optionally periodically during exploitation.

20. The method of claim 19, wherein the 90-degree optical hybrid calibration includes
   adjusting a coupling rate of a third coupler via a third control line from a controller to maximize a variance or minimize a mean of output I;
   adjusting a coupling rate of a fourth coupler via a fourth control line from a controller to maximize a variance or minimize a mean of output Q; adjusting the coupling rates of the first and second couplers via the first and second control lines to equalize the variance of I and Q outputs, while maximizing a sum of two variances at outputs I and Q.

* * * * *